United States Patent
Saito et al.

(10) Patent No.: US 8,040,504 B2
(45) Date of Patent: Oct. 18, 2011

(54) DEFECT INSPECTING METHOD AND DEFECT INSPECTING APPARATUS

(75) Inventors: Misako Saito, Nirasaki (JP); Teruyuki Hayashi, Nirasaki (JP); Kaoru Fujiwara, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 178 days.

(21) Appl. No.: 12/376,407

(22) PCT Filed: Aug. 7, 2007

(86) PCT No.: PCT/JP2007/065451
§ 371 (c)(1), (2), (4) Date: Feb. 4, 2009

(87) PCT Pub. No.: WO2008/018463
PCT Pub. Date: Feb. 14, 2008

(65) Prior Publication Data
US 2010/0245812 A1    Sep. 30, 2010

(30) Foreign Application Priority Data

Aug. 11, 2006 (JP) .................... 2006-220162

(51) Int. Cl.
*G01N 21/00* (2006.01)
(52) U.S. Cl. ............. 356/237.4; 356/237.5; 250/310
(58) Field of Classification Search .... 356/237.1–237.5, 356/239.1, 239.7, 239.8; 250/441.11, 492.2, 250/307, 310
See application file for complete search history.

(56) References Cited

U.S. PATENT DOCUMENTS

| | | | |
|---|---|---|---|
| 7,133,550 B2 * | 11/2006 | Hiroi et al. | 382/145 |
| 7,403,279 B2 * | 7/2008 | Tohyama et al. | 356/237.2 |
| 7,476,856 B2 * | 1/2009 | Watanabe et al. | 250/310 |
| 2003/0090651 A1 * | 5/2003 | Toyoshima et al. | 356/72 |
| 2005/0051721 A1 | 3/2005 | Watanabe et al. | |
| 2007/0285653 A1 * | 12/2007 | Takahashi et al. | 356/237.2 |
| 2008/0073524 A1 | 3/2008 | Nishiyama et al. | |
| 2008/0174772 A1 * | 7/2008 | Nara et al. | 356/237.5 |
| 2009/0050822 A1 * | 2/2009 | Nakasuji et al. | 250/492.2 |

FOREIGN PATENT DOCUMENTS

| | | |
|---|---|---|
| JP | 2005 17145 | 1/2005 |
| JP | 2005 61837 | 3/2005 |
| JP | 2007 235023 | 9/2007 |

OTHER PUBLICATIONS

Office Action issued Nov. 22, 2010, in Korean Patent Application No. 10-2009-7002675, filed Feb. 10, 2009 (with English translation).

* cited by examiner

*Primary Examiner* — Hoa Pham
(74) *Attorney, Agent, or Firm* — Oblon, Spivak, McClelland, Maier & Neustadt, L.L.P.

(57) ABSTRACT

Provided is a method and apparatus for inspecting a defect of a shape formed on a substrate. Primary inspection is sequentially performed on specific patterns in a plurality of divided regions of the substrate by using an optical method, and one or more regions on which secondary inspection is to be performed are selected from the regions. One or more defects are detected by performing the secondary inspection using an electron beam on the selected regions.

10 Claims, 6 Drawing Sheets

DEFECT INSPECTING METHOD AND DEFECT INSPECTING APPARATUS

FIELD OF THE INVENTION

The present invention relates to a defect inspection method and apparatus; and, more particularly, to a defect inspection method and apparatus using optical inspection and electron beam inspection.

BACKGROUND OF THE INVENTION

Various methods of inspecting pattern shapes for defects have been used as methods of inspecting semiconductor devices (semiconductor chips) on which patterns of various shapes are formed. For example, hitherto, a method of inspecting pattern shapes for defects using an optical inspection device (an optical inspection method) such as an optical microscope has been used. Meanwhile, as pattern shapes become finer, it is difficult to detect defects using only an optical method. Accordingly, there has been proposed a method of detecting the defects of fine pattern shapes using an electron beam in the inspection of pattern shapes for defects (see, for example, Japanese Patent Laid-open Publication No. 2005-61837).

The detection of defects using an electron beam has a problem in that inspection requires a long time. Accordingly, in consideration of the efficiency of inspection, the actual area that can be inspected is limited.

Japanese Patent Laid-open Publication No. 2005-61837 discloses a method in which the optical inspection and the electron beam inspection are combined together. However, this method is used merely to detect defects through the optical inspection of all patterns formed on a substrate and confirm the defects using the electron beam method. Accordingly, this method cannot overcome the problems that the efficiency of the detection of defects is low and the inspection of defects requires a long time.

SUMMARY OF THE INVENTION

It is, therefore, a general object of the present invention to provide a novel and useful defect detection method and apparatus capable of solving the above-described problems.

Specifically, the present invention provides a defect inspection method and apparatus capable of detecting the defects of a pattern shape formed on a substrate at high efficiency.

In accordance with an aspect of the present invention, there is provided a method for inspecting a defect of a shape formed on a substrate, including: a first step of sequentially performing primary inspection on specific patterns in a plurality of divided regions of the substrate using an optical method, and selecting one or more regions on which secondary inspection is to be performed from the plurality of regions; and a second step of detecting one or more defects by performing the secondary inspection using an electron beam on the regions selected in the first step.

In the method in accordance with the present invention, it is preferred that each of the regions be a region that corresponds to a single die when semiconductor chips are formed in the substrate. Alternatively, each of the regions may be a region that corresponds to a single semiconductor chip when semiconductor chips are formed in the substrate.

In the method according to the present invention, it is preferred that the specific patterns be test patterns that are respectively formed in the regions. Alternatively, the specific patterns may be memory cells that are respectively formed in the regions.

In the method according to the present invention, it is preferred that in the first step, the specific patterns be analyzed by radiating light onto the specific patterns and analyzing the spectra of light reflected from the specific patterns.

In addition, in accordance with another aspect of the present invention, there is provided an apparatus for inspecting a defect of a shape formed on a substrate, including: an optical inspection apparatus for sequentially performing primary inspection on specific patterns in a plurality of divided regions of the substrate using an optical method, and selecting one or more regions on which secondary inspection is to be performed from the plurality of regions; and an electron beam inspection apparatus for detecting one or more defects by performing the secondary inspection using an electron beam on the regions selected by the optical inspection apparatus.

In the method according to the present invention, it is preferred that the optical inspection apparatus analyze the specific patterns by radiating light onto the specific patterns and analyzing the spectra of light reflected from the specific patterns.

In accordance with the present invention, it is possible to provide a defect inspection method and apparatus capable of detecting the defects of a pattern shape formed on a substrate at high efficiency.

DESCRIPTION OF REFERENCE NUMERALS

100: optical inspection apparatus
100A: optical inspection unit
100B: control unit
100C: computer
101: radiation means
102: detection unit
103: light
104: reflected light
200: electron beam inspection apparatus
200A: electron beam inspection unit
200B: control unit
200C: signal processing unit
200D: display unit 200D
200E: image memory unit
200F: pattern matching unit
200G: memory unit
201: vacuum chamber
202: electron emission unit
203: convergence lenses
204: scanning coil 205: substrate support
206: electron detection unit
207: power source

DETAILED DESCRIPTION OF THE PREFERRED EMBODIMENTS

Figure 1:
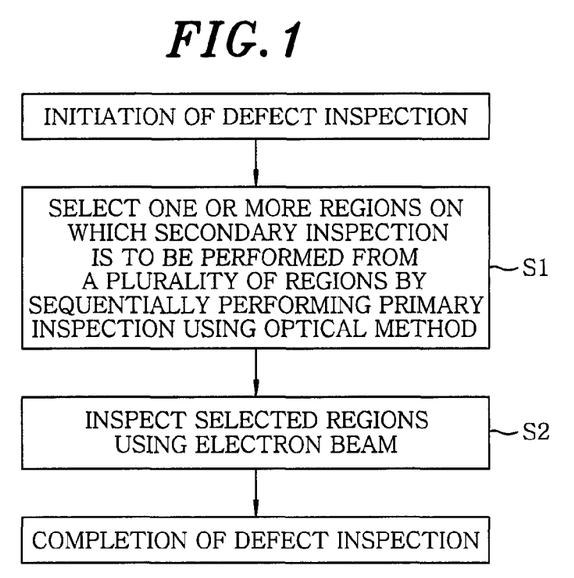
FIG. 1 is a flowchart showing a defect inspection method in accordance with an embodiment of the present invention.

First, a defect inspection method in accordance with an embodiment of the present invention will be described with reference to FIG. 1. FIG. 1 is a flowchart showing an outline of the defect inspection method in accordance with the embodiment of the present invention. The defect inspection method shown in FIG. 1 is a method of detecting one or more defects of a pattern shape (for example, a pattern wiring or a hole) formed on a substrate.

In the defect inspection method shown in FIG. 1, an optical primary inspection is performed at step S1. Thereafter, at step S2, secondary inspection using an electron beam is performed based on the results of the optical inspection. In the above-described primary inspection, one or more regions of the substrate in each of which there is a high possibility of defects existing therein are detected through optical inspection, and one or more regions on which secondary inspection using an electron beam capable of detecting one or more fine defects is to be performed is quickly selected.

In the above-described defect inspection method, in a plurality of regions which is formed to divide a substrate, one or more regions each having a high possibility of defects existing therein are quickly selected by sequentially inspecting the respective regions by using the optical method.

That is, the above-described primary inspection differs from a method of inspecting all patterns (shapes) on a substrate in principle (for example, the method disclosed in Japanese Patent Laid-open Publication No. 2005-61837), and determines whether a possibility of defects existing in each divided region is high or low by sequentially inspecting patterns respectively formed in the divided regions. As a result, one or more regions each having a high possibility of defects existing therein are selected, and secondary inspection using an electron beam capable of detecting one or more fine defects is performed on the selected regions.

Furthermore, in the performance of the above-described primary inspection, it is preferable to use a method of analyzing the shape of a specific pattern by radiating light (for example, laser light or the like) onto the specific pattern and analyzing the spectrum of light reflected from the specific pattern. An example of this analysis method will be described later.

As described above, the pattern recognition method based on reflected light analysis has an advantage in that the primary inspection efficiency thereof is better than the pattern recognition method using an optical microscope (for example, the method disclosed in Japanese Patent Laid-open Publication No. 2005-61837).

That is, the method based on the spectrum analysis of reflected light detects one or more defects by radiating light onto a specific pattern in a spot manner and analyzing reflected light, rather than detecting defects through scanning as does the pattern recognition method using an optical microscope. As a result, the method based on the spectrum analysis of reflected light has excellent primary inspection efficiency. Furthermore, since such radiation of light (the analysis of reflected light) can be performed on the portions of divided regions on which specific patterns are formed in a spot manner, it is possible to perform primary inspection at very high speed.

Furthermore, it is preferable to determine a plurality of regions obtainable through the division of a substrate by using, for example, the following method. Generally, in the manufacture of a semiconductor device (a semiconductor chip), a substrate is divided into a plurality of regions arranged in a matrix shape, called dies. Generally, in the formation of the semiconductor chip, a single unit at the time when exposure is performed using an exposure apparatus is referred to as a "die." A single die is sometimes called a single shot.

Accordingly, in the defect inspection method in accordance with the present embodiment, regions corresponding to the above-described dies are used as a plurality of divided regions used in the primary inspection. Defect inspection can be efficiently performed by setting a single region as a region corresponding to a single die as described above.

There are various reasons for the reduction in yield in the manufacture of semiconductor chips. It is thought that variation in exposure and development depending on patterning has a large influence on the reduction in yield. In this case, it is possible to efficiently detect one or more defects attributable to variation in exposure and development by determining a possibility of any defect existing in each die in such a way as to perform primary inspection on each die, which is a single shot in the case of exposure or development.

Figure 2:
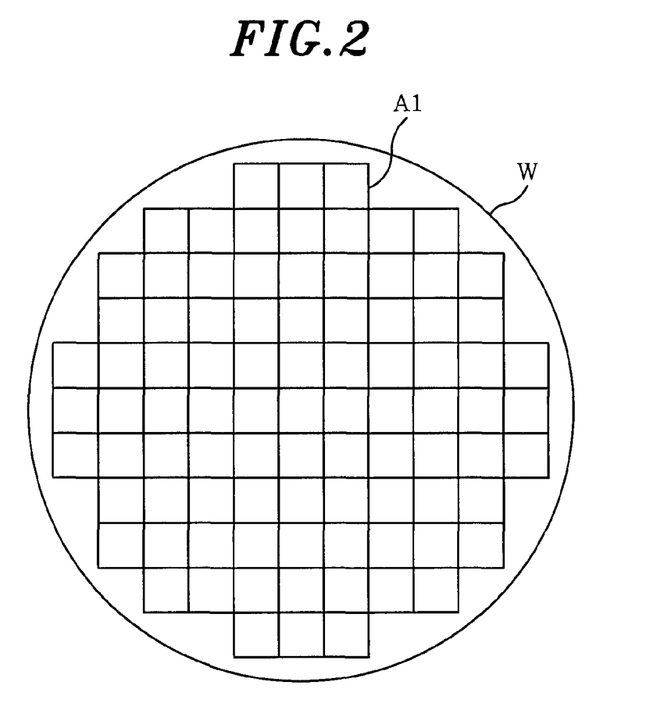
FIG. 2 is a diagram showing a plurality of divided regions on a substrate.

FIG. 2 is a schematic diagram showing an example in which a substrate W is divided into a plurality of regions (e.g., dies) A1. In FIG. 2, the regions A1 are arranged on the substrate W in a matrix shape. The primary inspection is performed on a specific pattern of each region A1 in a spot manner.

Figure 3:
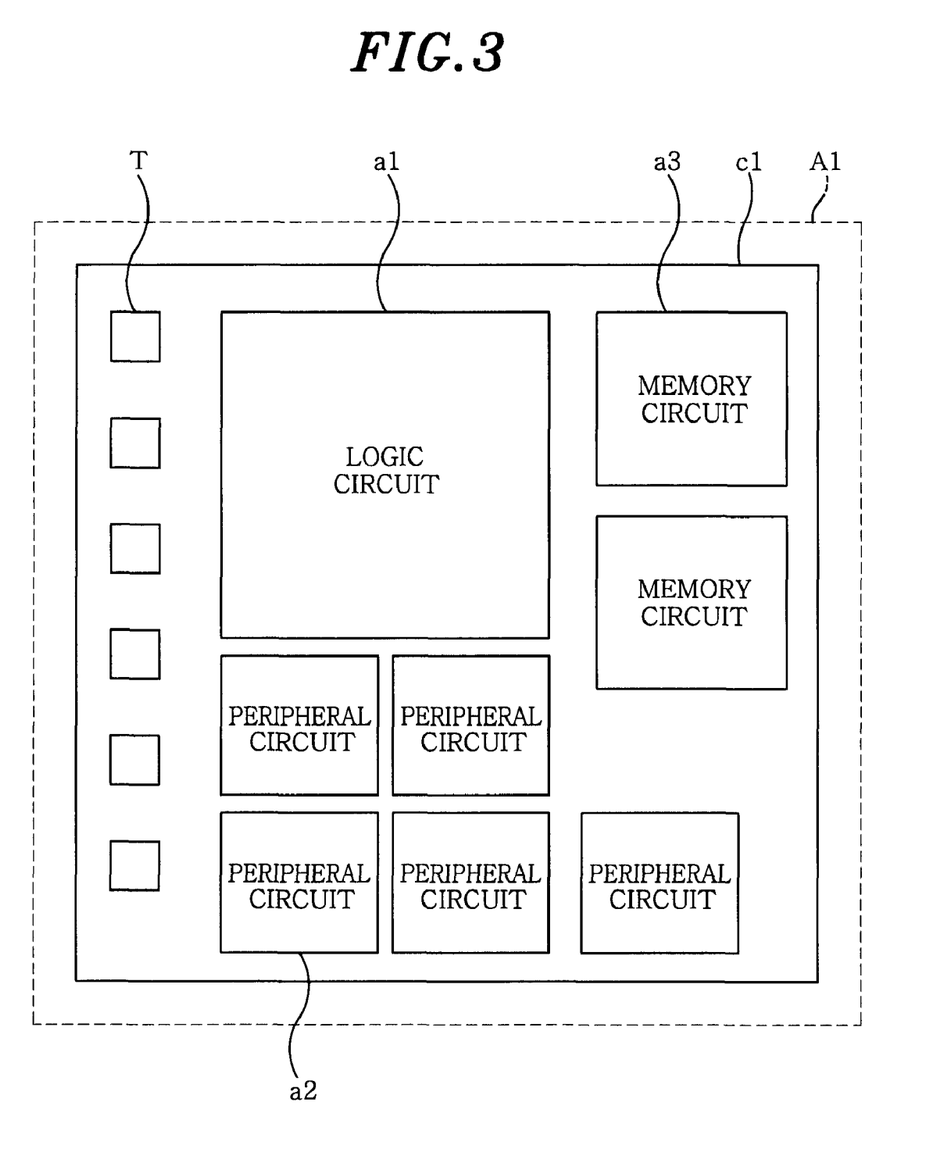
FIG. 3 is an enlarged view showing the region shown in FIG. 2.

FIG. 3 is an enlarged diagram schematically illustrating a region A1. FIG. 3 shows the case where one semiconductor chip C1 is formed on one die (region A1). Here, the semiconductor chip C1 is a logic semiconductor chip.

The semiconductor chip C1 is provided with a section a1 in which a logic circuit is formed, sections a2 in which peripheral circuits are formed, and sections a3 in which memory circuits are formed. Furthermore, sections T in which test patterns are formed are arranged along a peripheral edge portion of the semiconductor chip C1. The test patterns correspond to the specific pattern in the above-described primary inspection. For example, whether to perform secondary inspection using an electron beam on the region A1 is determined by performing optical inspection on the test patterns.

Furthermore, settings may be made such that a pattern (a primary inspection area on which the primary inspection is performed) that is the target of the primary inspection and a pattern (a secondary inspection area on which the secondary inspection is performed) that is the target of the secondary inspection using an electron beam may differ from each other.

For example, separate test patterns may be formed on a substrate so that a test pattern targeted for optical inspection is used in the primary inspection and a test pattern targeted for electron beam inspection is used in the secondary inspection.

Furthermore, in the secondary inspection, inspection may be performed using the pattern of the device of the semiconductor chip formed on, for example, any one of the sections a1 to a3 other than the test patterns.

In the primary inspection, fast inspection is performed using a test pattern with the highest priority given to efficiency in order to select a region on which the secondary inspection is to be performed. In contrast, in the secondary inspection, defect detection may be performed using the pattern of the device (section a1 to a3) based on the characteristics of a product (a semiconductor chip) with priority given to the precision of inspection.

Furthermore, in the above-described primary inspection, it is preferable to select a region for secondary inspection based on the difference between the design shape of the specific pattern used in the primary inspection and the shape actually obtained in the primary inspection.

That is, if in the region on which the inspection has been performed, the difference between the shape of the specific pattern obtained through the primary inspection and the design shape of the specific pattern is great, it is estimated that there is a high possibility of defects of the shape existing in the corresponding region. Accordingly, it is preferable to detect one or more finer defects by performing the secondary inspection on the corresponding region. In contrast, if in the region on which the primary inspection has been performed, the difference between the shape of the specific pattern obtained through the primary inspection and the design shape of the specific pattern is small, it is estimated that there is a low possibility of defects of the shape existing in the corresponding region, with the result that it is possible to omit the performance of the secondary inspection on the corresponding region.

For example, if the corresponding pattern is a linear pattern (pattern wiring) and the difference between the design width of a line in a certain region and the width of the line obtained through the primary inspection is equal to or greater than a predetermined value, the secondary inspection may be performed on the corresponding region.

Furthermore, if the corresponding pattern is a hole and the difference between the design diameter of the hole and the diameter of the hole obtained through the primary inspection is equal to or greater than a predetermined value, the secondary inspection may be performed on the corresponding region.

Furthermore, in the above-described primary inspection, one or more regions on which the secondary inspection is to be performed may be selected from a plurality of regions based on the difference in the shape of each pattern.

Figure 4:
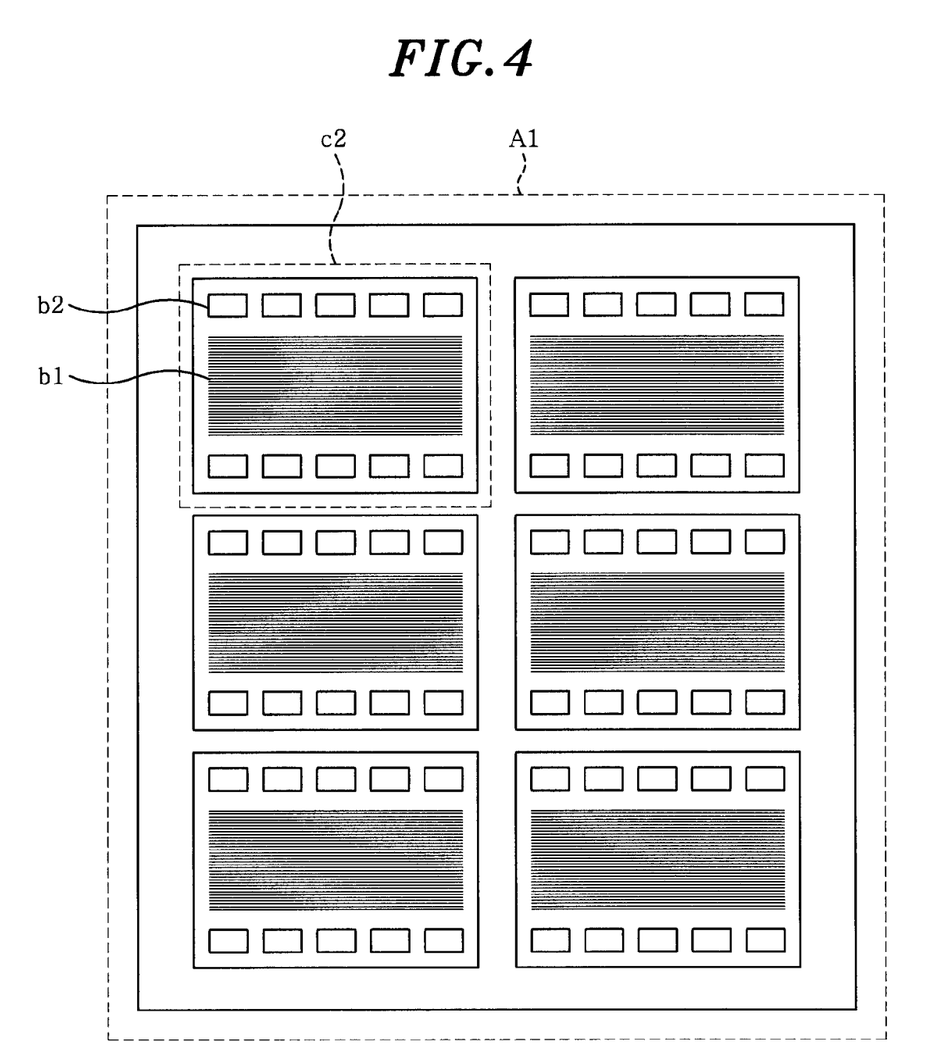
FIG. 4 is another enlarged view showing the region shown in FIG. 2.

Furthermore, the present invention is not limited to the case shown in FIG. 3, but various patterns or various devices may be formed on the region A1 of the substrate W. FIG. 4 is a diagram showing a different example of the region A1. In the example shown in FIG. 4, a plurality of memory type semiconductor chips C2 is formed in the region A1. Furthermore, a memory cell b1 and peripheral circuits b2 are formed in each of the semiconductor chips C2. As such, there is the case where a plurality of semiconductor chips is formed in a single die (a single region).

Furthermore, in the example shown in FIG. 4, the above-described memory cells b1 may be used as the specific pattern to be used in the primary inspection.

Furthermore, in the example shown in FIG. 4, the primary inspection may be performed on any one memory cell b1 of the plurality of semiconductor chips C2, for example, in a portion for each die. Furthermore, the primary inspection may be performed on respective semiconductor chips C2 inside one die. In this case, the primary inspection may be performed on the memory cell b1 of each semiconductor chip C2.

Thereafter, an example of the construction of a defect inspection apparatus for performing the above-described defect inspection method will be described with reference to FIGS. 5 to 7.

Figure 5:
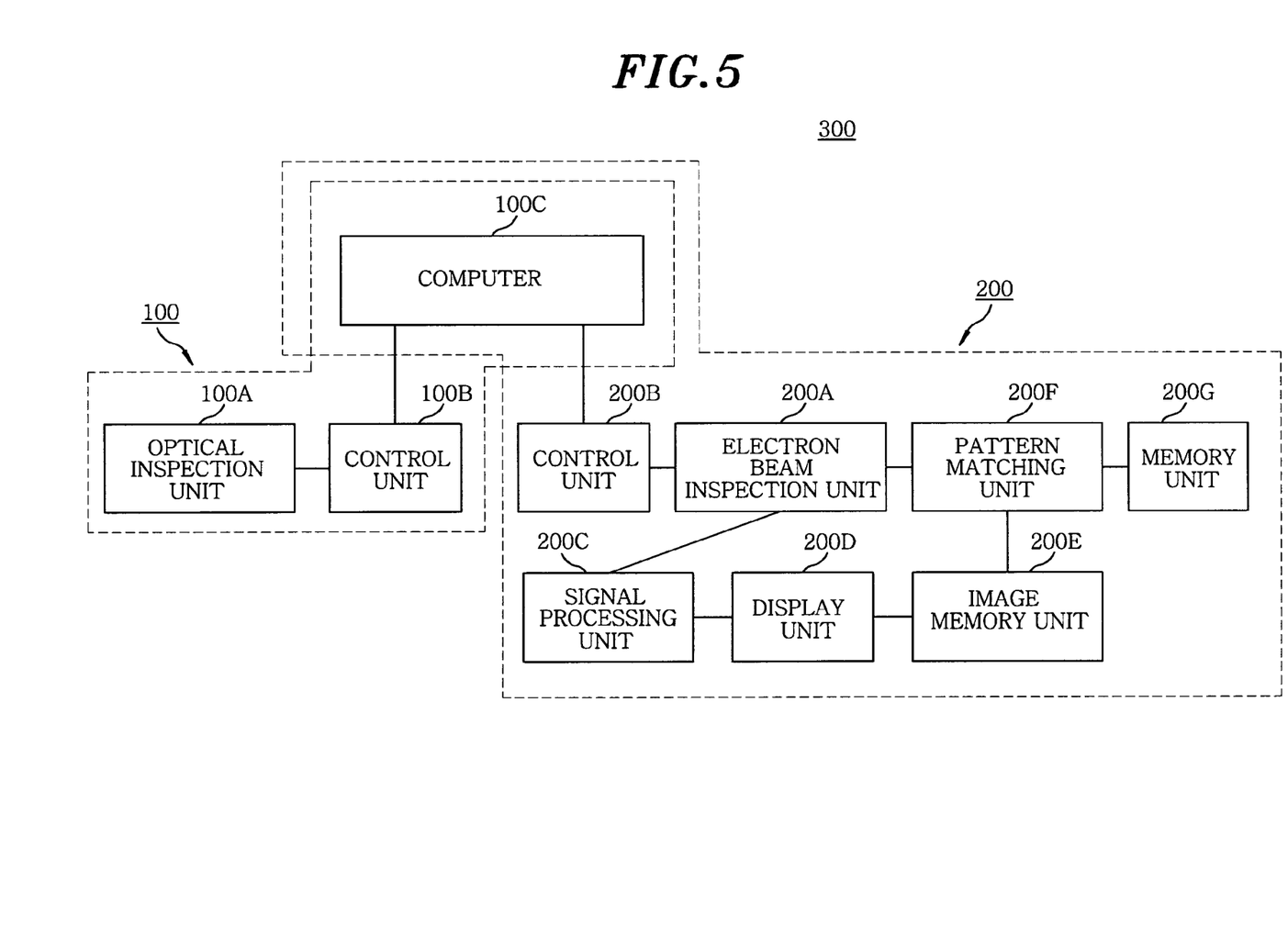
FIG. 5 is a diagram showing a defect inspection apparatus in accordance with an embodiment of the present invention.
Figure 6:
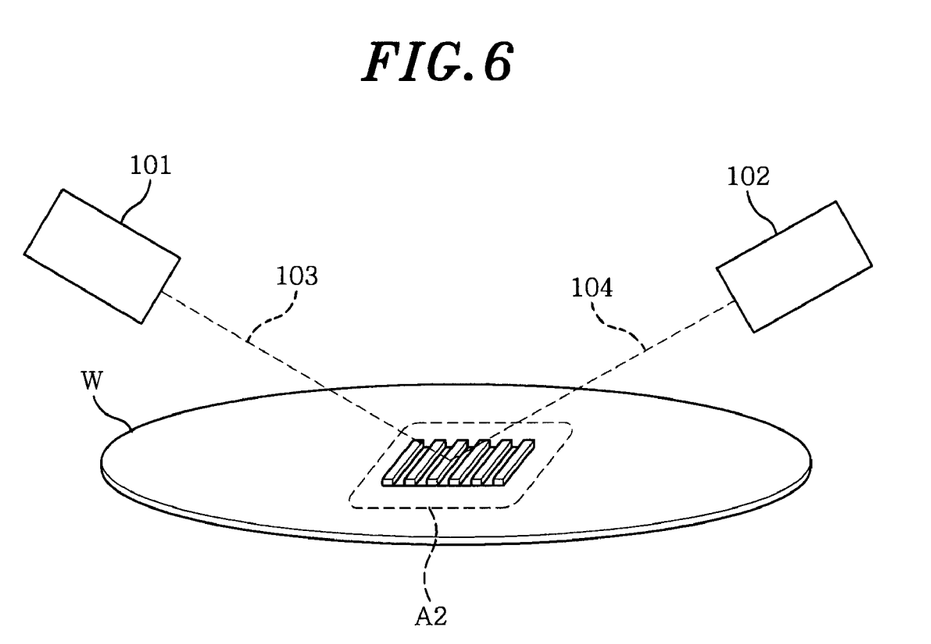
FIG. 6 is a diagram schematically showing an optical inspection method.

FIG. 5 is a diagram schematically showing the construction of the defect inspection apparatus for performing the defect inspection method shown in FIG. 1. The defect inspection apparatus 300 shown in FIG. 5 includes an optical inspection apparatus 100 and an electron beam inspection apparatus 200.

First, the optical inspection apparatus 100 will be described. The optical inspection apparatus 100 includes an optical inspection unit 100A, a control unit 100B, and a computer 100C. The optical inspection unit 100A recognizes the shape of a specific pattern by radiating light, such as laser light, onto the specific pattern on a substrate and analyzing light reflected from the specific pattern. The optical inspection unit 100A is operated by the computer 100C through the control unit 100B. Furthermore, the computer 100C is shared by the electron beam inspection apparatus 200, which will be described later. The primary inspection previously described in conjunction with FIG. 1 is performed by the above-described optical inspection apparatus 100, thereby selecting one or more regions on which the secondary inspection is to be performed.

Meanwhile, the electron beam inspection apparatus 200 includes an electron beam inspection unit 200A for radiating an electron beam onto a substrate (pattern), a control unit 200B, a signal processing unit 200C, a display unit 200D, an image memory unit 200E, a pattern matching unit 200F, a memory unit 200G, and the computer 100C shared by the optical inspection apparatus 100.

In the electron beam inspection unit 200A, an electron beam (primary electrons) is radiated onto the substrate (pattern) in a pressure-reduced space and secondary electrons created through the radiation of the primary electrons are detected. The data of the detected secondary electrons are processed into image data by the signal processing unit 200C. The image data are displayed on the display unit 200D. Furthermore, the image data are sequentially stored in the image memory unit 200E. One or more defects are detected by matching the image data and a comparison pattern with each other through the pattern matching unit 200F. Furthermore, the data of the detection of the defects is stored in the memory unit 200G when necessary.

As described above, in the electron beam inspection apparatus 200, it is possible to detect the defects of fine patterns, that are difficult to be detected in the optical inspection, by using an electron beam.

Hereinafter, the principle of the optical inspection apparatus 100 and the principle of the electron beam inspection apparatus 200 will be described with reference to the accompanying drawings.

First, the principle according to which the above-described optical inspection unit 100A recognizes the shape of a specific pattern will be described with reference to FIG. 6. The optical inspection unit 100A radiates light 103, such as laser light, onto the primary inspection area A2 of the specific pattern (for example, a test pattern or the like) of a substrate W using a radiation means 101, as shown in FIG. 6.

Here, the light 103 is reflected from the specific pattern. The reflected light 104 is detected by a detection unit 102, and is subjected to spectroscopic analysis using a spectroscope (not shown) such as a spectroscopic ellipsometer or a spectral radiometer. Here, the profile (the line width, hole diameter and height) of the above-described specific pattern can be calculated by comparing the spectrum pattern of the reflected light with a plurality of spectrum patterns (these are sometimes referred to as "library") previously stored in the computer 100C and selecting the most similar spectrum.

Such optical pattern recognition methods (apparatuses) are disclosed in, for example, Japanese Patent Laid-open Publication Nos. 2005-61837, 2002-243925 and 2005-517903. According to the above-described method, the primary inspection can be performed more efficiently than, for example, pattern recognition using an optical microscope.

Furthermore, according to the above-described method, for example, the angle of the pattern formed and surface roughness on the edges of the pattern as well as the line width and hole diameter of the pattern can be quickly calculated without performing complicated processing such as signal processing.

That is, since according to the above-described method, it is possible to quickly check the general status of the shape of a pattern in the primary inspection area A2 onto which the light 103 has been radiated, whether to perform the secondary inspection on the region in which the corresponding pattern has been formed can be quickly determined.

Thereafter, the electron beam inspection unit 200A of the electron beam inspection apparatus 200 will be schematically described with reference to FIG. 7. FIG. 7 is a diagram schematically showing the electron beam inspection unit 200A.

Figure 7:
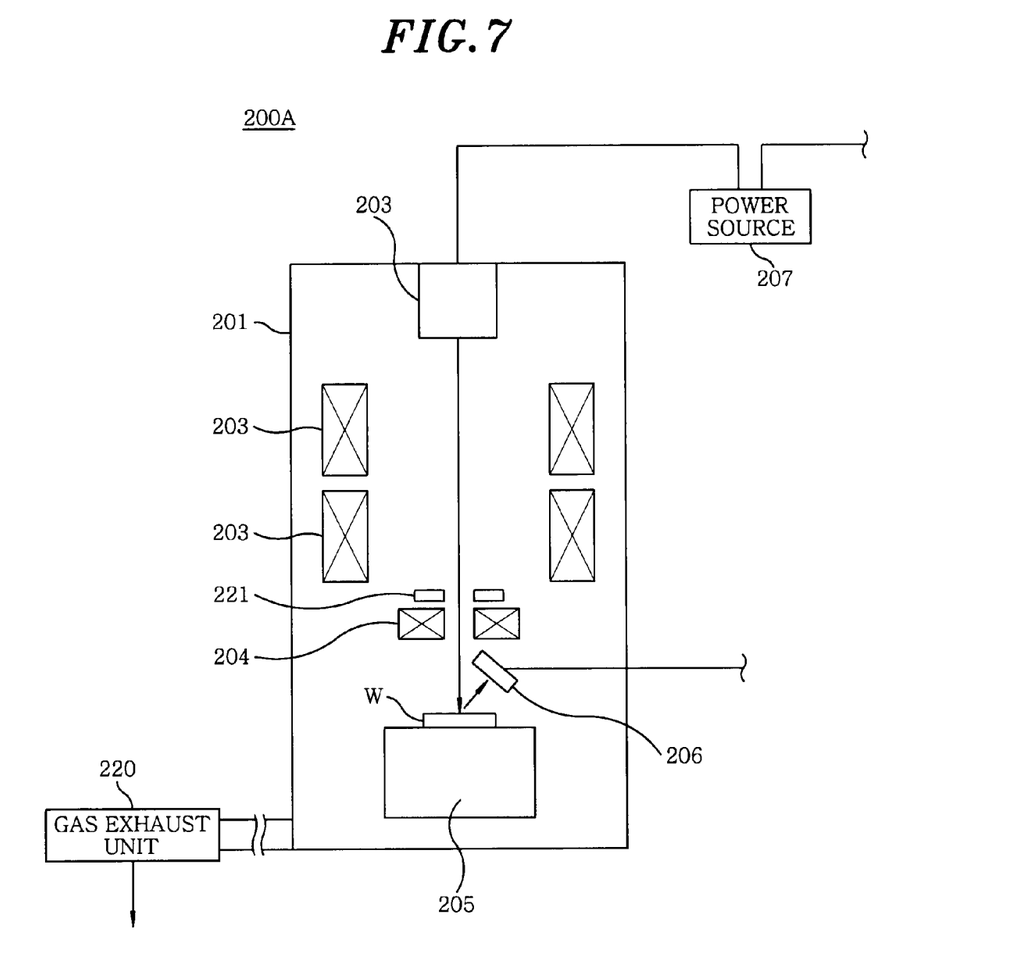
FIG. 7 is a diagram schematically showing an electron beam inspection method.

As shown in FIG. 7, the electron beam inspection unit 200A in accordance with the present embodiment includes a vacuum chamber 201 that is evacuated by a gas exhaust unit 220 to form a pressure-reduced space. A substrate support 205 for supporting a substrate W to be inspected is installed inside the vacuum chamber 201. Furthermore, an electron emission unit 202 for radiating primary electrons onto the substrate W is disposed opposite to the substrate support 205.

Furthermore, convergence lenses 203 for converging the emitted primary electrons (the electron beam), a scanning coil 204 for scanning the primary electrons, and an aperture 221 are disposed between the electron emission unit 202 and the substrate support 205. Furthermore, an electron detection unit 206 for detecting the secondary electrons created through the radiation of the primary electrons is disposed between the substrate support 205 and the scanning coil 204. A power source 207 for applying voltage to the electron emission unit 202 is connected to the electron emission unit 202.

In the electron beam inspection unit 200A, the primary electrons are radiated onto the substrate W by applying a predetermined voltage to the electron emission unit 202 from the power source 207. The secondary electrons created by the primary electrons radiated onto a pattern on the substrate W are detected by the electron detection unit 206, and are processed by the signal processing unit 200C shown in FIG. 5, thus forming image data.

The electron beam inspection unit 200A is sometimes referred to as "Scanning Electron Microscope (SEM) inspection apparatus."

As described above, the electron beam defect inspection can detect finer defects than in the optical defect inspection. However, the defect inspection using an electron beam has a problem in that the inspection of a wide area at high magnification requires a long time.

Accordingly, in the defect inspection apparatus 300, one or more regions of a substrate on which the secondary inspection using an electron beam is to be performed are quickly selected by performing primary inspection using the optical inspection apparatus 100. As a result, inspection for one or more fine defects can be performed at higher efficiency.

Furthermore, since in the defect inspection apparatus 300, the specific patterns in the divided regions of a substrate are inspected in a spot manner as described above, one or more regions that require the secondary inspection and each of which has a high possibility of defects existing therein can be quickly selected.

Furthermore, the above-described defect inspection method and apparatus can be applied to, for example, the manufacture of display devices, such as liquid crystal display devices and plasma display devices, and other electronic parts as well as the manufacture of semiconductor chips (semiconductor devices).

Although the preferred embodiments of the present invention have been described above, the present invention is not limited to the disclosed specific embodiments, and various modifications and variations can be made without departing from the scope of the present invention.

This application claims the benefit of Japanese Patent Application No. 2006-220162 filed on Aug. 11, 2006, the contents of which are hereby incorporated by reference in their entirety.

INDUSTRIAL APPLICABILITY

The present invention may be applied to an inspection method and apparatus for detecting defects using optical inspection and electron beam inspection.

What is claimed is:

1. A method for inspecting a defect of a shape formed on a substrate, comprising:
a first step of sequentially performing primary inspection on specific patterns in a plurality of divided regions of the substrate using an optical method, and selecting one or more divided regions on which secondary inspection is to be performed from the plurality of divided regions; and
a second step of detecting one or more defects by performing the secondary inspection using an electron beam on the divided regions selected in the first step,
wherein each of the plurality of divided regions includes multiple semiconductor chips, and the primary inspection is performed on a part of one semiconductor chip of each of the plurality of divided regions.

2. The method according to claim 1, wherein the specific patterns are memory cells that are formed in the plurality of divided regions.

3. The method according to claim 1 or 2, wherein in the first step, the specific patterns are analyzed by radiating light onto the specific patterns and analyzing spectra of light reflected from the specific patterns.

4. The method according to claim 1, wherein, in the second step, the secondary inspection using the electron beam is performed on patterns other than the specific patterns on which the primary inspection was performed.

5. The method according to claim 1, wherein each of the plurality of divided regions corresponds to a single die on which exposure is performed at a time.

6. An apparatus for inspecting a defect of a shape formed on a substrate including a plurality of divided regions, each of the plurality of divided regions having a plurality of semiconductor chips, the apparatus comprising:
an optical inspection apparatus for sequentially performing primary inspection on specific patterns in the plurality of divided regions of the substrate using an optical method, and selecting one or more divided regions on which secondary inspection is to be performed from the plurality of divided regions; and
an electron beam inspection apparatus for detecting one or more defects by performing the secondary inspection using an electron beam on the divided regions selected by the optical inspection apparatus,
wherein the optical inspection apparatus performs the primary inspection on a part of one semiconductor chip of each of the plurality of divided regions.

7. The apparatus according to claim 6, wherein the optical inspection apparatus analyzes the specific patterns by radiating light onto the specific patterns and analyzing spectra of light reflected from the specific patterns.

8. The apparatus according to claim 6, wherein the specific patterns are memory cells that are formed in the plurality of divided regions.

9. The apparatus according to claim 6, wherein the electron beam inspection apparatus performs the secondary inspection on patterns other than the specific patterns on which the primary inspection was performed.

10. The apparatus according to claim 6, wherein each of the plurality of divided regions corresponds to a single die on which exposure is performed at a time.

* * * * *